United States Patent
Ishizaki et al.

(10) Patent No.: US 11,578,183 B2
(45) Date of Patent: Feb. 14, 2023

(54) RESIN COMPOSITION, METHOD FOR PRODUCING RESIN COMPOSITION, RESIN COMPOSITION MOLDED BODY, AND METHOD FOR PRODUCING RESIN COMPOSITION MOLDED BODY

(71) Applicant: SOMAR CORPORATION, Tokyo (JP)

(72) Inventors: Hirohisa Ishizaki, Tokyo (JP); Akira Ochiai, Tokyo (JP)

(73) Assignee: SOMAR CORPORATION, Tokyo (JP)

( * ) Notice: Subject to any disclaimer, the term of this patent is extended or adjusted under 35 U.S.C. 154(b) by 652 days.

(21) Appl. No.: 16/463,401

(22) PCT Filed: Nov. 27, 2017

(86) PCT No.: PCT/JP2017/042426
§ 371 (c)(1),
(2) Date: May 23, 2019

(87) PCT Pub. No.: WO2018/097292
PCT Pub. Date: May 31, 2018

(65) Prior Publication Data
US 2019/0309143 A1    Oct. 10, 2019

(30) Foreign Application Priority Data
Nov. 28, 2016   (JP) .............. JP2016-230424

(51) Int. Cl.
| | |
|---|---|
| *C08K 3/22* | (2006.01) |
| *B29C 35/02* | (2006.01) |
| *C08J 3/09* | (2006.01) |
| *C08K 9/04* | (2006.01) |
| *C08L 101/00* | (2006.01) |
| *C08K 5/00* | (2006.01) |
| *C08K 3/00* | (2018.01) |
| *C08F 2/46* | (2006.01) |
| *C08L 15/00* | (2006.01) |
| *C08L 63/00* | (2006.01) |
| *C08L 67/04* | (2006.01) |
| *C08L 75/04* | (2006.01) |
| *C08L 83/04* | (2006.01) |
| *C08L 63/08* | (2006.01) |
| *C07C 255/54* | (2006.01) |

(52) U.S. Cl.
CPC .............. *C08K 3/22* (2013.01); *B29C 35/02* (2013.01); *C08F 2/46* (2013.01); *C08J 3/092* (2013.01); *C08K 3/00* (2013.01); *C08K 5/00* (2013.01); *C08K 9/04* (2013.01); *C08L 101/00* (2013.01); *C01P 2006/42* (2013.01); *C07C 255/54* (2013.01); *C08K 2003/2265* (2013.01); *C08K 2201/01* (2013.01); *C08L 15/005* (2013.01); *C08L 63/00* (2013.01); *C08L 63/08* (2013.01); *C08L 67/04* (2013.01); *C08L 75/04* (2013.01); *C08L 83/04* (2013.01)

(58) Field of Classification Search
CPC .......... C08J 3/28; C08J 3/247; C08J 2379/02; C08K 3/013; C08K 3/08; C08K 2003/0862; C08K 2003/0843; C08K 2003/0831; C08K 2003/085; C08K 3/20; C08K 3/22; C08K 2003/22687; C08K 2003/2265; C08K 2201/001; C08K 2201/011; C08K 2201/01; C08K 2201/005; C08L 64/07; C08L 75/04; C08L 83/04; C08L 63/00; C08L 15/005
See application file for complete search history.

(56) References Cited

U.S. PATENT DOCUMENTS

| | | | |
|---|---|---|---|
| 4,409,300 | A | 10/1983 | Ohkawa et al. |
| 2005/0112409 | A1 | 5/2005 | Murayama et al. |
| 2005/0112410 | A1 | 5/2005 | Mori et al. |
| 2008/0220291 | A1 | 9/2008 | Nakir et al. |
| 2009/0087869 | A1 | 4/2009 | Fujimoto et al. |
| 2011/0319538 | A1* | 12/2011 | Thetford ............... C09D 7/45 524/145 |
| 2012/0249375 | A1* | 10/2012 | Heino .................. B05D 3/06 343/700 MS |
| 2013/0053471 | A1 | 2/2013 | Studart et al. |

(Continued)

FOREIGN PATENT DOCUMENTS

| | | |
|---|---|---|
| CN | 102618018 A | 8/2012 |
| CN | 103467997 A | 12/2013 |

(Continued)

OTHER PUBLICATIONS

Extended European Search Report (EESR) dated Jun. 2, 2020, The Analyst, vol. 135, No. 10, Jan. 1, 2010, pp. 1-6.
Chang-Yeoul Kim et al., "Magnetic Silicone Composites with Uniform Nanoparticle Dispersion as a Biomedical Stent Coating for Hyperthermia", Advances in Polymer Technology., vol. 32, No. S1, Oct. 8, 2012, pp. E714-E723.
Japanese Office Action for Application No. 2018-553002 dated Oct. 6, 2020, pp. 1-9 (English Translation Included).

(Continued)

*Primary Examiner* — Jane L Stanley
(74) *Attorney, Agent, or Firm* — Thomas|Horstemeyer, LLP

(57) ABSTRACT

A resin composition including: a magnetic fluid that includes magnetic particles, a dispersant, and a dispersion medium; and a resin or precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms, a production method thereof, a resin composition molded body obtained by using the resin composition, and a production method thereof.

13 Claims, No Drawings

(56) References Cited

U.S. PATENT DOCUMENTS

| | | | |
|---|---|---|---|
| 2013/0063296 A1* | 3/2013 | Hennig | H01Q 1/245 342/1 |
| 2016/0055947 A1 | 2/2016 | Pagano et al. | |
| 2016/0163437 A1 | 6/2016 | Ishizaki et al. | |

FOREIGN PATENT DOCUMENTS

| | | |
|---|---|---|
| CN | 104804299 A | 7/2015 |
| JP | H03-163805 A | 7/1991 |
| JP | H04-025102 A | 1/1992 |
| JP | H11-236506 A | 8/1999 |
| JP | 2000-012313 A | 1/2000 |
| JP | 2000-012314 A | 1/2000 |
| JP | 2000-293845 A | 10/2000 |
| JP | 2001-256639 A | 9/2001 |
| JP | 2003-026924 A | 1/2003 |
| JP | 2005-053980 A | 3/2005 |
| JP | 2005-129141 A | 5/2005 |
| JP | 2005-129150 A | 5/2005 |
| JP | 2005-332854 A | 12/2005 |
| JP | 2009-087467 A | 4/2009 |
| JP | 2013-525137 A | 6/2013 |
| JP | 2014-114431 A | 6/2014 |
| JP | 2015-169881 A | 9/2015 |
| JP | 2016-027538 A | 2/2016 |
| JP | 2016-114849 A | 6/2016 |
| JP | 2016-519430 A | 6/2016 |
| JP | 2016-127280 A | 7/2016 |
| KR | 10-2016-0033140 A | 3/2016 |
| KR | 2016-0061106 A | 5/2016 |
| WO | 2015/008842 A1 | 1/2015 |
| WO | 2016/104534 A1 | 6/2016 |

OTHER PUBLICATIONS

International Search Report for WO2018/097292 (PCT/JP2017/042426), dated Jan. 9, 2018, pp. 1-6.
Chinese Office Action for Application No. 201780073181.2 dated Mar. 3, 2021, pp. 1-15 (Partial English Translation Included).
Taiwanese Office Action for Application No. 106141358 dated Aug. 11, 2021, pp. 1-7 (English Translation Included).
Chinese Office Action for Application No. 201780073181.2 dated May 6, 2022, pp. 1-35 (Machine Translation Included).
Korean Office Action for Application No. 10-2019-7017654 dated Dec. 9, 2021, pp. 1-16 (English Translation Included).

* cited by examiner

US 11,578,183 B2

RESIN COMPOSITION, METHOD FOR PRODUCING RESIN COMPOSITION, RESIN COMPOSITION MOLDED BODY, AND METHOD FOR PRODUCING RESIN COMPOSITION MOLDED BODY

CROSS-REFERENCE TO RELATED APPLICATIONS

This application is the National Stage of International Application No. PCT/JP2017/042426, filed Nov. 27, 2017, which claims priority to JP2016-230424, filed Nov. 28, 2016, which are entirely incorporated herein by reference.

TECHNICAL FIELD

The present disclosure relates to a resin composition, a method for producing a resin composition, a resin composition molded body, and a method for producing a resin composition molded body.

BACKGROUND ART

In recent years, magnetic fluid has attracted attention as a magnetic material that is free of hysteresis and is usable in magnetic cores, rectifiers, electric current sensors, and the like. Magnetic fluid is a magnetic material that exhibits superparamagnetism imparted by dispersing a magnetic powder, such as ferrite particles or magnetite particles, having a particle diameter within a range of from 3 nm to 50 nm, in a dispersion medium such as isoparaffin or water. In order to exhibit superparamagnetism, the magnetic particles are required to have a particle diameter of a nanometer order. Further, in order to uniformly disperse such magnetic particles having a particle diameter of a nanometer order in a dispersion medium, covering of at least a part of the surface of the magnetic particles with a dispersant selected from surfactants or the like is generally performed.

By adding a magnetic fluid having fluidity to a curable resin composition, a molded body utilizing the characteristics of the magnetic fluid is obtained, and application of such a molded body in various fields of application, where magnetic properties are required, can be expected.

For example, in trying to obtain a resin composition through mixing a magnetic fluid and a resin material, for the purpose of using the resulting resin composition for a magnetic core, a rectifier, or an electric current sensor, the magnetic particles may aggregate at the time of removing the dispersion medium included in the magnetic fluid. When an aggregate of magnetic particles is formed, there are cases in which the resin composition including the magnetic particles has magnetic hysteresis or the aggregate causes phase separation. Therefore, by only mixing a magnetic fluid and a resin material, there are cases in which a resin composition that is provided for practical use for forming a molded body cannot be obtained.

As a means to eliminate this disadvantage, the applicant of the present application has proposed a magnetic powder composition that includes a resin material and a magnetic powder obtained by removing a dispersion medium from a magnetic fluid containing magnetic particles, a dispersant, and the dispersion medium, a magnetic powder composition molded body which is a cured body of the magnetic powder composition, and production methods thereof (see, for example, International Publication No. 2015/008842).

SUMMARY OF INVENTION

Technical Problem

However, according to the method described in International Publication No. 2015/008842, it is necessary to go through a process of obtaining a magnetic powder from a magnetic fluid in order to obtain a magnetic powder composition. Therefore, there is room for improvement in terms of work efficiency.

An object according to an embodiment of the present invention is to provide a resin composition, which includes a magnetic fluid and a resin, in which aggregation of magnetic particles is suppressed, and which is free of magnetic hysteresis caused by aggregation of magnetic particles, and a production method thereof.

An object according to another embodiment of the present invention is to provide a resin composition molded body, which is a cured body of a resin composition including a magnetic fluid and a resin and which is free of magnetic hysteresis, and a production method thereof.

Solution to Problem

Means for addressing the above problems include the following embodiments.

<1> A resin composition including: a magnetic fluid that includes magnetic particles, a dispersant, and a dispersion medium; and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms.

<2> The resin composition according to <1>, wherein the resin is at least one thermosetting resin selected from the group consisting of an epoxy resin, a silicone resin and a polyurethane resin.

<3> The resin composition according to <2>, wherein the epoxy resin is at least one selected from the group consisting of a rubber-modified epoxy resin, a dimer acid-modified epoxy resin, a trimer acid-modified epoxy resin and a silicone-modified epoxy resin.

<4> The resin composition according to <1>, wherein the precursor includes at least one selected from the group consisting of a polyol and an alkenyl group-containing organo polysiloxane.

<5> The resin composition according to any one of <1> to <4>, wherein the content of the dispersion medium with respect to the total amount of the resin composition is 5% by mass or less.

<6> The resin composition according to any one of <1> to <5>, further including at least one selected from the group consisting of a curing agent and a cross-linking agent.

<7> The resin composition according to any one of <1> to <6>, further including a resin or a precursor thereof that does not include, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms.

<8> The resin composition according to any one of <1> to <7>, wherein the content of the resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms, and an alkylene group having from 6 to 30 carbon atoms, with respect to the total content of resins or precursors thereof incorporated in the resin composition is from 10% by mass to 100% by mass.

<9> A resin composition molded body that is a cured body of the resin composition according to any one of <1> to <8>.

<10> A method for producing a resin composition, the method including: a process of preparing a resin mixture including a magnetic fluid that includes magnetic particles, a dispersant, and a dispersion medium, and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms; and a process of heating the resin mixture to remove the dispersion medium.

<11> A method for producing a resin composition molded body, the method including: a process of preparing a resin mixture including a magnetic fluid that includes magnetic particles, a dispersant, and a dispersion medium, and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms, and an alkylene group having from 6 to 30 carbon atoms; a process of heating the resin mixture to remove the dispersion medium; and a process of heat molding the resin mixture from which the dispersion medium has been removed.

Although the mechanism working in the resin composition according to the present disclosure is not clearly understood, it is thought that the mechanism is as follows.

In a magnetic fluid having excellent magnetic properties, fine magnetic particles are dispersed in a dispersion medium by using a dispersant. The dispersant, such as a surfactant, forms interaction with the magnetic particles, whereas the dispersant also has affinity with the dispersion medium. Therefore, in the case of heating a mixture of the magnetic fluid and a resin material, as it is, and removing the dispersion medium, to obtain a resin composition, curing inhibition may occur in the resin material. It is thought that this curing inhibition is caused by the dispersion medium that is adsorbed to the magnetic fluid through the dispersant.

In the resin composition according to the present disclosure, the resin or precursor thereof, which coexists with the magnetic fluid, includes at least one partial structure (hereinafter, may be referred to as "specific partial structure") selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms, in a molecule thereof. Since these specific partial structures impart a moderate flexibility to the resin, the distance between the cross-links in the cross-linked structure, which is formed at the time of curing the resin, is adjusted to be within a moderate range. Accordingly, it is thought that, at the time of curing the resin or the precursor thereof, the magnetic particles are stably held between the cross-linked structures that have been formed and thus, aggregation is suppressed.

Therefore, in the process of removing the dispersion medium in the magnetic fluid by heating, the magnetic fluid, that is, the magnetic particles whose circumstance is covered with the dispersion medium are present in a state of being uniformly dispersed in the resin mixture. Here, the hydrophobic specific partial structure possessed by the resin material and the hydrophobic dispersion medium that is present around the magnetic particles form some interaction, whereby the resin material is adsorbed on the surface of the magnetic particles through the dispersant. It is presumed that, in the state in which the resin material is adsorbed to the magnetic particles, by heating to vaporize and remove the dispersion medium, or the like, the amount of the dispersion medium remaining in the system gets extremely small, and thus, curing inhibition with respect to the resin material due to the remaining of the dispersion medium is suppressed.

Further, in the resin composition, the magnetic particles that exhibit magnetic properties in the magnetic fluid are uniformly dispersed to leave spaces with each other in the base resin material, similar to the case of being dispersed in the dispersion medium. Therefore, it is presumed that, in the case of preparing a molded body using the resin composition, the molded body thus obtained has magnetic properties similar to those in the case of using the magnetic fluid.

Note that, the mechanism working in the resin composition is not limited to the above presumption.

Advantageous Effects of Invention

According to an embodiment of the invention, a resin composition, which includes a magnetic fluid and a resin, in which aggregation of magnetic particles is suppressed, and which is free of magnetic hysteresis caused by the aggregation of magnetic particles, and a production method thereof may be provided.

According to another embodiment of the invention, a resin composition molded body, which is a cured body of a resin composition including a magnetic fluid and a resin and which is free of magnetic hysteresis, and a production method thereof may be provided.

DESCRIPTION OF EMBODIMENTS

Hereinafter, the resin composition according to the present disclosure and the like are described in detail. However, the explanation of constituent elements described below is one example (a representative example) of embodiments of the invention, and the embodiments are not limited to the contents of the explanation. The invention may be practiced with various modifications within the scope of the gist of the invention.

Note that, in this specification, a numerical range expressed using "to" represents a range including numerical values described in front of and behind "to", as the minimum value and the maximum value, respectively.

In this specification, in a case in which plural substances corresponding to a component are included in a composition, the amount of the component included in the composition means the total amount of the plural substances, unless specified otherwise.

In this specification, in the numerical ranges described step by step, the upper limit value or the lower limit value described in one numerical range may be replaced with the upper limit value or the lower limit value of other numerical ranges described step by step. Further, in a numerical range described in this specification, the upper limit value or the lower limit value of the numerical range may be replaced with the value shown in the Examples.

In this specification, the combination of preferable forms is a more preferable form.

Further, the expression "substituent" is used in a sense including an unsubstituted form thereof and a form further having a substituent, unless specified otherwise. For example, the expression "alkyl group" as used herein is intended to include both an unsubstituted alkyl group and an alkyl group further having a substituent. The same applies to other substituents.

In this specification, the term "process" includes not only an independent process, but also a case which cannot be clearly distinguished from other process, as long as the predetermined action is achieved.

In this specification, in a case in which plural substances corresponding to a component are present in a composition, the amount of the component in the composition means the total amount of the plural substances that exist in the composition, unless specified otherwise.

[Resin Composition]

The resin composition according to the present disclosure is a resin composition including a magnetic fluid that includes magnetic particles, a dispersant, and a dispersion medium; and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms.

Note that, in this specification, the term "a resin or a precursor thereof" in the resin composition is used in a sense including a form in which the resin composition includes only a resin, a form in which the resin composition includes only a precursor of a resin, and a form in which the resin composition includes both a resin and a precursor of the resin.

In the resin composition according to the present disclosure, the state of the magnetic particles that exist in the state of being dispersed in the magnetic fluid is maintained, and the resin composition exhibits superparamagnetism similar to that of the magnetic fluid. Therefore, the resin composition molded body described below, which is a cured body of the resin composition, exhibits superparamagnetism as well.

Note that, in this specification, the term "superparamagnetism" refers to a magnetic characteristic possessed by an aggregate of fine particles of a ferromagnetic substance, and means a nature of not exhibiting magnetic hysteresis and not having remanent magnetization. The superparamagnetism of the resin composition according to the present disclosure exhibits from 100-fold to 100,000-fold higher atomic magnetic moment, as compared with the atomic magnetic moment of paramagnetism.

The resin composition according to the present disclosure includes a magnetic fluid that includes magnetic particles, a dispersant, and a dispersion medium, and a resin or a precursor thereof that includes a specific partial structure described above.

By reducing the content of the dispersion medium incorporated in the resin composition according to the present disclosure, a resin composition which is further suitable for the formation of a resin composition molded body can be obtained.

Hereinafter, each component included in the resin composition is described.

[1. Magnetic Fluid]

The magnetic fluid which can be used in the resin composition according to the present disclosure includes magnetic particles, a dispersant, and a dispersion medium. In general, a magnetic fluid is a colloidal liquid in which magnetic particles are dispersed in a dispersion medium by using a dispersant. The dispersibility of the magnetic particles in the magnetic fluid is excellent, and solid-liquid separation such as precipitation or separation of magnetic particles due to, for example, the gravitational force or a magnetic field does not occur. Thus, the fluid itself can be regarded as a uniform liquid having magnetism.

The magnetic fluid to be used in the present disclosure may be prepared as appropriate, or a commercially available product may be used as the magnetic fluid.

Examples of the commercially available product include EXP series, P series, APG series, and REN series (trade names, all manufactured by Ferrotec Corporation).

In the case of preparing a magnetic fluid, examples of the preparation method include a method of reducing the sizes of macroscopic magnetic particles into colloidal sizes, and a method of condensing atoms or ions to obtain fine magnetic particles.

Examples of the method of reducing the sizes of magnetic particles include a pulverization method and a spark erosion method. Examples of the method of condensing atoms or ions include a chemical co-precipitation method (wet method), a method of thermally decomposing a metal carbonyl, and a vacuum deposition method.

Among them, as a method for preparing a magnetic fluid, a chemical co-precipitation method is preferable in terms of achieving excellent productivity.

An example of a method of preparing a magnetic fluid by a chemical co-precipitation method is a method including adding sodium oleate to a magnetite water slurry prepared by using an aqueous solution of iron (II) sulfate and an aqueous solution of iron (III) sulfate, to cause oleic acid ions to be adsorbed on the surface of the magnetite particles, thereby obtaining particles, then washing the obtained particles with water, followed by drying, and then dispersing the resulting particles in an organic solvent, that is, a dispersion medium.

Hereinafter, each component which can be contained in the magnetic fluid according to the present disclosure is described.

(Magnetic Particles)

Examples of the magnetic particles contained in the magnetic fluid include ferromagnetic oxides; ferromagnetic metals; and metal nitrides.

Examples of the ferromagnetic oxides include magnetite, γ-iron oxide, manganese ferrite, cobalt ferrite, a composite ferrite of any of these with at least one of zinc or nickel, and barium ferrite. Examples of ferromagnetic metals include iron, cobalt, and rare earth elements. Among them, as the magnetic particles, magnetite is preferable from the viewpoint of mass productivity.

The magnetic particles for use in the present disclosure are used without particular limitation as long as the magnetic particles have an average particle diameter within a range in which superparamagnetism is exhibited, that is, an average particle diameter which is equal to or less than the critical particle diameter. For example, in the case of magnetite particles or γ-iron oxide particles, the average particle diameter is preferably 50 nm or less, and particularly preferably in a range of from 10 nm to 40 nm.

From the viewpoint of mass productivity, the content of magnetic particles contained in the magnetic fluid is preferably from 30% by mass to 70% by mass, and more preferably from 40% by mass to 60% by mass, with respect to the total mass of the magnetic fluid.

Note that, the above content of magnetic particles refers to a content calculated from the mass of the magnetic particles in which a dispersant is adhered on at least a part of the surface thereof.

(Dispersant)

A dispersant is added in order to improve the dispersibility of the magnetic particles in the dispersion medium. As the dispersant, a known surfactant, a polymeric dispersant, or the like can be used as appropriate. Among them, from the viewpoints of dispersibility and the performance of the resulting magnetic powder, a surfactant is preferable.

When the above magnetic particles and a dispersant are included in a magnetic fluid, at least a part of the dispersant adheres to the magnetic particles, as a result of which, at least a part of the surface of the magnetic particles is covered with a dispersant, preferably a surfactant. Accordingly, hydrophilic groups of the surfactant are adhered toward the surface of the magnetic particles, and hydrophobic groups of the surfactant are oriented toward the dispersion medium side, so that the magnetic particles are stably dispersed in the dispersion medium.

Examples of the surfactant which may be used as the dispersant in the present disclosure include: anionic surfactants, which are hydrocarbon compounds having a polar group such as a carboxyl group, a hydroxyl group, or a sulfonic acid group, for example, oleic acid or a salt thereof, a petroleum sulfonic acid or a salt thereof, a synthetic sulfonic acid or a salt thereof, eicosyl naphthalene sulfonic acid or a salt thereof, polybutene succinic acid or a salt thereof, erucic acid or a salt thereof, and the like; nonionic surfactants, for example, polyoxyethylene nonyl phenyl ether, and the like; and amphoteric surfactants, which have both a cationic moiety and an anionic moiety in the molecular structure thereof, for example, alkyl diamino ethyl glycine, and the like. Among them, a sodium salt of oleic acid (hereinafter, may be referred to as "sodium oleate") is preferable as the dispersant, from the viewpoints of its low price and easy availability.

The magnetic fluid may contain only one kind of dispersant, or may contain two or more kinds thereof.

The total content of the dispersant in the magnetic fluid is not particularly limited as long as the total content is an amount with which aggregation between magnetic particles can be prevented. The total content of the dispersant may be selected as appropriate in accordance with the intended use.

The content of the dispersant can be set to be, for example, from 3% by mass to 30% by mass, and is preferably from 5% by mass to 20% by mass, with respect to the total amount of the magnetic fluid.

In the magnetic fluid, the dispersant is adsorbed to the magnetic particles and, as a result, at least a part of the surface of the magnetic particles is in a state of being covered with the dispersant. From the viewpoint of preventing aggregation between magnetic particles, it is preferable that a dispersant of from about 1 nm to about 5 nm is adsorbed on the surface of the magnetic particles, and it is more preferable that a dispersant of about 2 nm to about 3 nm is adsorbed on the surface of the magnetic particles.

Regarding the average particle diameter of the magnetic particles covered with a dispersant, in a case in which the magnetic particles are magnetite or γ-iron oxide, the average primary particle diameter is preferably 55 nm or less, and more preferably in a range of from 11 nm to 45 nm, in consideration of the preferable particle diameter of the magnetic particles described above.

Note that, in this specification, hereinafter, the average primary particle diameter of the magnetic particles indicates the average particle diameter of the magnetic particles in which a surfactant is covered with a dispersant, unless specified otherwise.

In this specification, the average primary particle diameter of the magnetic particles is a value measured using a nano particle analyzer NANO PARTICA SZ-100 series manufactured by Horiba Ltd. in accordance with a dynamic light scattering method.

(Dispersion Medium)

The dispersion medium in the magnetic fluid is not particularly limited as long as the dispersion medium is in the liquid state at ordinary temperature (at 25° C.) and the magnetic particles can be dispersed therein.

Examples of the dispersion medium include water and organic solvents. One or two or more selected from the group consisting of water and organic solvents can be used.

Examples of the organic solvents include: hydrocarbons having a molecular weight of 5,000 or less, such as polyolefins, isoparaffin, heptane, or toluene; esters such as polyol esters; and silicone oils. As long as the mutual solubility is favorable, plural kinds of organic solvents may be mixed and used.

Note that, the expression "the mutual solubility is favorable" indicates that phase separation does not occur, after mixing plural kinds of organic solvents, stirring the mixture, and then allowing the resulting mixture to stand still at 25° C. for 1 hour.

Further, water, a mixture of water and a water-soluble organic solvent, or the like may also be used preferably.

Examples of the water-soluble organic solvent include ethanol and methanol. In the case of using water as the dispersion medium, it is preferable to use pure water, in which the content of impurities is small, ion exchange water, or the like.

There is no particular limitation on the concentration of each component with respect to the dispersion medium. From the viewpoints of working property in producing a resin composition using a resin mixture, and the like, it is preferable that the dispersion medium is contained in an amount such that the solid matter concentration as a total of the respective components described above, which are incorporated in the resin mixture, is in a range of from 30% by mass to 90% by mass, and it is more preferable that the dispersion medium is contained in an amount such that the solid matter concentration is in a range of from 60% by mass to 80% by mass.

Regarding the solid matter contained in the magnetic fluid, the ratio of the total content of the magnetic particles (inorganic components) relative to the total content of organic components such as a dispersant typified by a surfactant is not particularly limited as long as the ratio is within the range in which the magnetic fluid exhibits superparamagnetism. In general, the mass ratio of the magnetic particles to the dispersant, namely, (magnetic particle content:dispersant content) is preferably in a range of from 60:40 to 90:10, and more preferably in a range of from 70:30 to 85:15.

The ratio of the content of the inorganic components relative to the content of the organic components in the magnetic fluid can be verified by differential heat-heat capacity measurement. In this specification, regarding the content of each component, a numerical value obtained by a measurement using an EXSTAR6000TG/DTA manufactured by Seiko Instruments Inc. (SII) is adopted.

(Additional Components)

In the magnetic fluid, in addition to the magnetic particles, the dispersant, and the dispersion medium, various additional components may further be used in accordance with the purposes, within a range in which the effects of the invention are not impaired.

Examples of the additional components include a pH adjusting agent such as potassium hydroxide or triethylamine. Inclusion of a pH adjusting agent enables the control of dispersibility of the magnetic particles.

[2. Resin that Includes, in a Molecule Thereof, at Least One Partial Structure (Specific Partial Structure) Selected from the Group Consisting of a Diene Skeleton, a Silicone Skeleton, a Urethane Skeleton, a 4- to 7-Membered Ring Lactone Skeleton, an Alkyl Group Having from 6 to 30 Carbon Atoms and an Alkylene Group Having from 6 to 30 Carbon Atoms, or Precursor Thereof]

The resin composition according to the present disclosure includes a resin or a precursor thereof that includes a specific partial structure in a molecule thereof. By the inclusion of at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms, as a specific partial structure, the resin or the precursor thereof may have a so-called soft segment inside the resin, due to the specific partial structure. By the presence of the soft segment between the joining structures, such as cross-links, which are formed at the time of curing the resin in the resin composition, the distance between the joining structures is adjusted to be within a moderate range, and the magnetic particles are each held in the space between the joining structures. Accordingly, it is thought that, at the time of curing the resin, aggregation of magnetic particles, which may occur due to a decrease in the amount of the solvent or dispersion medium, a progress of the curing reaction, or the like, is suppressed, or, the occurrence of curing inhibition, which is caused by the dispersion medium that is adsorbed to the magnetic particles through the dispersant, is suppressed.

Further, it is thought that, in a case in which the resin composition contains a thermoplastic resin, at the time of removing the solvent by heating, the magnetic particles are held while spaced from each other in the soft segment region that exists in the molecule of the thermoplastic resin and, as a result, aggregation of magnetic particles, which may occur with a decrease in the amount of the solvent or dispersion medium or with the progress of the curing reaction, is suppressed.

It is enough that the resin or the precursor thereof has a specific partial structure, and the specific partial structure may be included in any part of the resin.

That is, the specific partial structure may be included in the main skeleton of the resin, or in a case in which the resin has a side chain structure, the specific partial structure may be included in the side chain.

Further, the specific partial structure may be introduced afterwards in the resin. Specifically, by using a resin precursor including a specific partial structure, as the raw material of the resin, the specific partial structure may be introduced into the molecule of the resin at the time of formation of the resin. Furthermore, the specific partial structure may be introduced into the main skeleton of the resin through a polymerization reaction.

(Specific Partial Structure)
1. Diene Skeleton

The diene skeleton in this specification indicates a structure having two double bonds in the skeleton.

Examples of a compound having the diene skeleton include a homopolymer or copolymer of a conjugate diene compound, a partially hydrogenated substance of any of these; and a rubber component. Examples of the rubber component include rubber components of nitrile butadiene rubber (NBR), carboxyl group-terminated modified butadiene nitrile rubber (CTBN), butadiene rubber, acrylic rubber, or the like. Among them, nitrile butadiene rubber (NBR) and carboxyl group-terminated modified butadiene nitrile rubber (CTBN) are preferable.

2. Silicone Skeleton

The silicone skeleton in this specification indicates a structure having a siloxane bond. The siloxane bond means an —Si—O— unit. In this specification, it is preferable that the silicone skeleton has a moiety in which 1 to 1000 of this unit are repeatedly integrated. The silicone skeleton may be any substance that has a siloxane bond. Accordingly, an organo polysiloxane, in which an organic group is bonded to a siloxane bond, is also included. Examples of the organic group include an alkyl group such as a methyl group, an ethyl group, a propyl group, or a butyl group, a cycloalkyl group such as a cyclohexyl group, an alkenyl group such as a vinyl group or an allyl group, and an aryl group such as a phenyl group or a tolyl group. Among them, a vinyl group-containing organo polysiloxane is preferable.

3. Urethane Skeleton

The urethane skeleton in this specification indicates a structure including a urethane bond in the main chain. The urethane bond is obtained through the reaction of a polyisocyanate and a polyol. Examples of the polyisocyanate include TDI (toluene diisocyanate), MDI (diphenylmethane diisocyanate), NDI (naphthalene diisocyanate), TODI (tolidine diisocyanate), HDI (hexamethylene diisocyanate), and IPDI (isophorone diisocyanate). Examples of the polyol include polyester polyol, polyether polyol, polyesteramide polyol, acrylic polyol, polyhydroxyalkane, a nature oil polyol, and polyurethane polyol.

4. 4- to 7-Membered Ring Lactone Skeleton

The lactone skeleton in this specification indicates a structure having an ester group in the ring. Examples of the 4- to 7-membered ring lactone skeleton include β-propiolactone (4), γ-valerolactone, δ-valerolactone (5, 6), δ-caprolactone, and ε-caprolactone (6, 7). Among the above lactone skeletons, ε-caprolactone is preferable. Note that, the number in the parenthesis described together with the above compound indicates the number of members that constitute the lactone skeleton.

5. Alkyl Group Having from 6 to 30 Carbon Atoms, and Alkylene Group Having from 6 to 30 Carbon Atoms Each of the alkyl group and the alkylene group, as the specific partial structure, has 6 or more carbon atoms, and preferably 7 or more carbon atoms. Further, each of the alkyl group and the alkylene group has 30 or less carbon atoms, preferably 24 or less carbon atoms, and more preferably 18 or less carbon atoms.

The alkyl group or the alkylene group, as the specific partial structure, may be a straight chain or may have a branched chain, as long as the alkyl group or the alkylene group has carbon atoms within the range described above.

Each of the alkyl group and the alkylene group, as the specific partial structure, preferably has from 6 to 24 carbon atoms, more preferably from 7 to 24 carbon atoms, and still more preferably from 7 to 18 carbon atoms.

Examples of the alkyl group having from 6 to 30 carbon atoms include a hexyl group, an octyl group, a decyl group, a dodecyl group, a hexadecyl group, an eicosyl group, a docosyl group, a tetracosyl group, an octacosyl group, and a triacontyl group.

Examples of the alkylene group having from 6 to 30 carbon atoms include a hexylene group, an octylene group, a decylene group, a dodecylene group, a hexadecylene group, an eicosylene group, a docosylene group, a tetracosylene group, an octacosylene group, and a triacontylene group.

Each of the above alkyl group and the above alkylene group may have a substituent.

For example, partial structures derived from a fatty acid, which is an alkyl group having an acid group as a substituent, or a derivative thereof are also included in the scope of the specific partial structure in this specification.

The above fatty acid in the scope of the specific partial structure may be a saturated fatty acid or may be an unsaturated fatty acid.

Further, at least one selected from the group consisting of a partial structure derived from a dimer acid prepared by dimerizing unsaturated fatty acids and a partial structure derived from a trimer acid prepared by trimerizing unsaturated fatty acids is also included in the scope of the specific partial structure described above.

Examples of a compound including an unsaturated fatty acid capable of forming a specific partial structure include linderic acid, tsuzuic acid, physetoleic acid, myristoleic acid, zoomaric acid, petroselinic acid, oleic acid, elaidic acid, gadoleic acid, gondoic acid, whale oil acid, erucic acid, brassidic acid, selacholeic acid, linoleic acid, linoelaidic acid, linolenic acid, and eleostearic acid.

The resin or the precursor thereof in the resin composition according to the present disclosure is not particularly limited, except that the resin or the precursor thereof has a specific partial structure. The resin or the precursor thereof can be selected as appropriate in accordance with the intended uses of the resin composition and the resin composition molded body which is a cured body of the resin composition.

The resin incorporated in the resin composition may be a thermosetting resin or a thermoplastic resin.

Examples of the thermosetting resin include an epoxy resin, a phenol resin, a melamine resin, a polyimide resin, a urea resin, an unsaturated polyester resin, a polyurethane resin, and a silicone resin. Among them, at least one thermosetting resin selected from the group consisting of an epoxy resin, a silicone resin and a polyurethane resin, or a precursor of any of these is preferable.

Examples of the thermoplastic resin include an acrylic resin, a polyethylene resin, an olefin resin, a polypropylene resin, a polyvinyl chloride resin, a polyvinyl acetate resin, an acrylonitrile butadiene styrene copolymer resin, and a polytetrafluoroethylene resin such as TEFLON (registered trademark). Among them, at least one thermoplastic resin selected from the group consisting of an olefin resin and an acrylic resin is preferable.

In addition, specific examples of the specific partial structure include: polyalkylene glycol including an alkylene group having from 2 to 5 carbon atoms, for example, polyethylene glycol, polypropylene glycol, or the like; a long chain polyol such as polyoxyalkylene glycol including an alkylene group having from 2 to 5 carbon atoms; and a copolymer of (meth)acrylate and a radical polymerizable monomer selected from ethylene, vinyl acetate, or (meth) acrylic ester.

The specific partial structure may be included in a precursor of the thermosetting resin or the thermoplastic resin.

When a precursor of a resin includes a specific partial structure, a resin obtained from the precursor has the specific partial structure in a molecule thereof.

Examples of the precursor of a resin having a specific partial structure include a polyol and an alkenyl group-containing organo polysiloxane.

A polyol is a precursor of a urethane resin. Examples of the polyol include polyester polyol, polyether polyol, polyesteramide polyol, acrylic polyol, polyhydroxyalkane, a nature oil polyol, and polyurethane polyol.

An alkenyl group-containing organo polysiloxane is a precursor of a silicone resin. Examples of the alkenyl group include a vinyl group, an aryl group, a butenyl group, a pentenyl group, a hexenyl group, and a heptenyl group.

Note that, in this specification, a resin containing a specific partial structure or a precursor thereof may be referred to as, simply, "a resin and a precursor thereof". Further, a resin containing a specific partial structure or a precursor thereof may be described using the name of the resin or the name of a modified resin with the name of the specific partial structure.

In the case of using the resin composition for applications in which heat resistance is considered to be important, the resin containing a specific partial structure is preferably an epoxy resin containing a specific partial structure or a silicone resin containing a specific partial structure, from the viewpoint of the strength of the resulting resin composition molded body.

Examples of the epoxy resin containing a specific partial structure include an aliphatic group-modified epoxy resin, a butadiene based epoxy resin; a caprolactone modified epoxy resin; a rubber-modified epoxy resin having, as the specific partial structure, a rubber such as NBR, CTBN, polybutadiene, or an acrylic rubber; a silicone modified epoxy resin; a dimer acid-modified epoxy resin; a trimer acid-modified epoxy resin; a urethane-modified epoxy resin; and a polyol-modified epoxy resin.

Examples of the silicone resin containing a specific partial structure include a silicone resin obtained through an addition reaction using an alkenyl group-containing organo polysiloxane, and a higher fatty acid modified silicone resin.

In the case of using the resin composition as an adhesive, it is preferable that the resin containing a specific partial structure includes an acrylic resin, a urethane resin, an epoxy resin, or the like.

Examples of the acrylic resin containing a specific partial structure may include copolymers containing (meth)acrylate and a radically polymerizable monomer such as ethylene, vinyl acetate, or (meth)acrylic ester.

Examples of the urethane resin containing a specific partial structure may include those containing the above-described long chain polyol as the specific partial structure.

Examples of the epoxy resin containing a specific partial structure may include the same epoxy resins as those exemplified above in the case of using the resin composition for applications in which heat resistance is considered to be important.

The resin composition may include only one kind of a resin containing a specific partial structure or a precursor thereof, or may contain two or more kinds thereof (Resin that does not Include Specific Partial Structure or Precursor Thereof)

The resin composition may include a resin or a precursor thereof that does not include a specific partial structure (hereinafter, may be referred to as "additional resin").

Examples of the additional resin include an epoxy resin, a phenol resin, a melamine resin, a polyimide resin, a urea resin, an unsaturated polyester resin, and a polyurethane resin, each of which does not include the specific partial structure described above.

In adding the resin or the precursor thereof to the resin composition, there is no particular limitation as to the form of the resin or the precursor thereof. The resin or the precursor thereof may be added in the form of a solid, for example, a pellet state, a powder state, or the like, or may be added in the form of a liquid state.

For example, a precursor of a resin has a low molecular weight and may be in the form of a liquid state. Examples of the resin in the form of a liquid state may include a resin which has been thermally melted to be in the liquid state, and a resin which is dissolved in an appropriate solvent to be in the liquid state.

(Content of Resin or Precursor Thereof)

The total content of the resin or a precursor thereof containing a specific partial structure with respect to the total mass of resins or precursors thereof incorporated in the resin composition is preferably from 10% by mass to 100% by mass, on the basis of mass ratio, and more preferably from 15% by mass to 90% by mass.

When the total content of the resin or a precursor thereof containing a specific partial structure with respect to the total mass of resins or precursors thereof incorporated in the resin composition is 10% by mass or higher, the magnetic particles which exhibit magnetic properties in the magnetic fluid are uniformly dispersed to leave spaces with each other in the base resin material, also in the resin composition, similar to the case of being dispersed in the dispersion medium in the magnetic fluid and, as a result, the resin composition and a cured body of the resin composition are likely to exhibit superparamagnetism, which is thus preferable.

(Content of Magnetic Particles)

The content of the magnetic particles in the resin composition according to the present disclosure is selected as appropriate in accordance with the intended use of the resin composition.

For example, in the case of using a resin composition molded body prepared by curing the resin composition for a sensor or the like, the content of the magnetic particles with respect to the total amount of the resin composition molded body is preferably from 50% by mass to 80% by mass. Further, in the case of using the resin composition for a magnetic coating material, an adhesive having magnetism, or the like, the content of the magnetic particles is preferably in a range of from 20% by mass to 40% by mass. Moreover, in the case of using the resin composition for a magnetic ink, the content of the magnetic particles is preferably from 5% by mass to 15% by mass.

(Content of Dispersion Medium)

The content of the dispersion medium with respect to the total mass of the resin composition according to the present disclosure is preferably 5% by mass or less. When the content of the dispersion medium is 5% by mass or less, the curing property is more favorable in the case of using the resin composition for producing a molded body.

Further, when the content of the dispersion medium is 5% by mass or less, occurrence of voids is suppressed in forming a resin composition molded body.

[3. Additional Components]

In addition to the magnetic fluid and the resin or a precursor thereof containing a specific partial structure, various components (additional components) may further be included in the resin composition in accordance with the purposes, within a range in which the effects are not imparted.

Examples of the additional components include a curing agent, a curing accelerator, a cross-linking agent, a softening agent, a coloring agent, a filler, a mold-releasing agent, and a flame retardant.

The resin composition can include at least one selected from a curing agent or a cross-linking agent.

When the resin composition includes at least one selected from a curing agent or a cross-linking agent, the curing reaction of the resin incorporated in the resin composition is accelerated.

As the curing agent or the cross-linking agent, a compound suitable for the resin or precursor thereof to be used may be selected and used.

Examples of the curing agent which may be used in the resin composition include an amine based compound, an imidazole based compound, an imidazoline based compound, a urea based compound, an acid anhydride based compound, an amide based compound, a hydrazide based compound, a phenol based compound, and a polysulfide based compound.

Examples of the cross-linking agent which may be used in the resin composition include sulfur, a sulfur compound, selenium, magnesium oxide, lead(II) oxide, an organic peroxide, polyamine, oxime, a nitroso compound, an alkylphenol-formaldehyde resin, a melamine-formaldehyde condensation product, an ammonium salt, and an H—Si group-containing organo polysiloxane.

The content of the curing agent with respect to 1 equivalent weight of the functional group incorporated in the whole resin or precursor thereof to be used is preferably from 0.6 equivalent weight to 1.2 equivalent weight.

There is no particular limitation on the method for producing the resin composition according to the present disclosure. For example, the resin composition described above is preferably produced by the method for producing the resin composition according to the present disclosure, which is described below.

Hereinafter, the method for producing the resin composition according to the present disclosure is described.

[Method for Producing Resin Composition]

The resin composition according to the present disclosure can be produced by a method for producing a resin composition, the method including a process (process A) of preparing a resin mixture including a magnetic fluid that includes magnetic particles, a dispersant, and a dispersion medium, and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms, and a process (process B) of heating the resulting resin mixture to remove the dispersion medium.

[1. Process A]

In process A, prescribed amounts of the magnetic fluid, the resin or a precursor thereof having a specific partial structure, and the additional components that are incorporated if desired are weighed out and placed in a vessel, followed by stirring and mixing them sufficiently to prepare a resin mixture.

The process A in the method of preparing a resin mixture includes, for example, supplying the resin or a precursor thereof having a specific partial structure, and the additional components that are incorporated if desired to the magnetic fluid, stirring, and mixing. The content of the magnetic fluid and the content of the resin or a precursor thereof having a specific partial structure in the resin mixture are each selected as appropriate in accordance with the physical properties of the intended resin composition or resin composition molded body.

In general, it is preferable that the resin or a precursor thereof having a specific partial structure are contained in an amount of from 20 parts by mass to 500 parts by mass with respect to 100 parts by mass of the magnetic fluid.

[2. Process B]

Process B includes: heating the resin mixture obtained in the above process A to remove the dispersion medium; and after removing the dispersion medium, cooling the resulting mixture to obtain a resin composition. By going through the process B, the content of the dispersion medium in the resin mixture is reduced and, as a result, the production of a resin composition molded body, which is carried out afterwards if desired, becomes easier.

There is no particular limitation as to the method of removing the dispersion medium. Examples of the method include a method of heating the resin mixture to a temperature around the boiling point of the dispersion medium or equal to or higher than the boiling point of the dispersion medium to evaporate and remove the dispersion medium, and the like.

The temperature for heating and the heating time are selected as appropriate in accordance with the physical properties of the dispersion medium included in the magnetic fluid.

In general, water, a mixture of water and an organic solvent such as isoparaffin, an organic solvent such as isoparaffin, or the like is used as the dispersion medium in the magnetic fluid. Accordingly, in removing the dispersion medium, the temperature for heating is preferably in a range of from 60° C. to 100° C., and more preferably in a range of from 80° C. to 90° C.

The heating time is preferably from 10 minutes to 60 minutes, and more preferably from 20 minutes to 40 minutes. In the process B, it is preferable to continuously perform stirring during heating, from the viewpoint of achieving efficient removal of the dispersion medium.

In the process B, the amount of the dispersion medium in the resin mixture is reduced and the dispersion medium is removed. It is not necessary to completely remove the dispersion medium from the resin mixture, and the dispersion medium may remain in the resin mixture as long as the amount of the dispersion medium is an amount that does not impair the curing property of the resin composition to be obtained through the process B. From the viewpoint of the effect, it is preferable that 95% by mass or more of the total amount of the dispersion medium incorporated in the resin composition at the time of preparing the resin composition obtained in the process A is removed in the process B.

The content of the dispersion medium in the resin composition obtained through the process B is preferably 5% by mass or less with respect to the total amount of the resin composition, as described above.

It is preferable that cooling of the resin mixture that has been heated is performed until the temperature of the resin mixture gets to room temperature (25° C.). The method for cooling is not particularly limited. An example of the method for cooling is a method of leaving the resin mixture under an environment of room temperature, thereby allowing the resin mixture to cool down.

The method for producing the resin composition according to the present disclosure has the process A and process B described above. In order to impart physical properties, that are suitable for the intended use of the resin composition, to the resin composition, at least one additional process other than the above-described processes may be included, within a range in which the effects are not impaired.

An example of the additional process is a process (process C) of adding at least one of the additional additives described above, such as a curing agent, to the resin composition from which the dispersion medium has been removed in the process B. Further, for example, in the case of adding a coloring agent to the resin composition, prior to the process (process A) of preparing a mixture, a process (process D) of mixing a coloring agent and a resin or a precursor thereof containing a specific partial structure may be included.

[3. Optional Process]

(Process C)

Process C is a process which is provided if desired. Process C is a process of adding at least one optional additive, such as a curing agent, to the resin composition which is obtained through the process B.

(Additional Components Included in Resin Composition)

As described above, the resin composition can include additional components.

The timing of adding the additional component which can be used in the resin composition is selected as appropriate in accordance with the properties of the additional component and the purpose of addition.

The additional component may be added to the resin mixture in the process A, may be added, prior to the process A, to the resin or a precursor thereof including a specific partial structure, before being used for preparing a mixture (process D), or may be added to the resin composition to be used for molding in the process of forming a molded body, which is described below (process C).

For example, from the viewpoint of uniformity, it is preferable to add a coloring agent or the like to the resin mixture in the process of preparing a mixture, or to the resin or the precursor thereof before being used for preparing a mixture.

A mold-releasing agent, as the additional component, is useful for the improvement in mold-releasing property of the molded body. Among the additional components which contribute to the production suitability and physical properties of the resin composition molded body, as typified by a mold-releasing agent, and the like, there are components which are more preferably added to the resin composition in the process of forming a molded body, which is described below, rather than to the resin mixture in the process A of preparing a mixture.

The resin composition containing magnetic particles, which is obtained by the method for producing a resin composition according to the present disclosure, does not have magnetic hysteresis, and maintains superparamagnetism. Accordingly, the resin composition is useful for the production of a molded body.

[Resin Composition Molded Body]

The resin composition molded body according to the present disclosure is a cured body of the above-described resin composition according to the present disclosure. The resin composition molded body is a molded body equipped with an excellent superparamagnetism possessed by the resin composition according to the present disclosure, the resin composition including a magnetic fluid.

[Method for Producing Resin Composition Molded Body]

The resin composition molded body according to the present disclosure can be produced by a production method including a process (process A) of preparing a resin mixture including a magnetic fluid that includes magnetic particles, a dispersant, and a dispersion medium, and a resin or a precursor thereof that includes, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms, a process (process B) of heating the resin mixture to remove the dispersion medium, and a process (process E) of heat molding the resin mixture from which the dispersion medium has been removed.

Note that, in the method for producing a resin composition molded body according to the present invention, the process (process A) of preparing a resin mixture, the process (process B) of removing the dispersion medium, and the processes (process C and process D) of adding at least one additive such as a curing agent, each of the processes C and D being conducted if desired, are substantially the same as the process A to the process D in the above-described method for producing a resin composition according to the present disclosure, respectively.

(Process E)

In process E, the resin composition obtained through the process B and, further, the process (process C) of adding a curing agent, which is carried out if desired, is heated according to the properties of the resin or precursor thereof incorporated in the resin composition, and molded, to obtain an intended resin composition molded body.

As the method for forming the resin composition molded body, various molding methods may be employed in accordance with the properties of the resin or precursor thereof to be used.

Examples of the molding methods include injection molding, compression molding, and dipping molding. There is no particular limitation as to the shape of the resin composition molded body obtained by such a molding method.

The temperature for heating and the heating time are each adjusted in accordance with the properties of the resin or precursor thereof incorporated in the resin composition.

In the process E of forming a molded body, at least one of the "additional components" described above can be further added to the resin composition in accordance with the purposes.

For example, in the case of forming a resin composition molded body using a metal mold, it is preferable to add a mold-releasing agent to the resin composition.

Since the resin composition molded body, which is obtained by the method for producing a resin composition molded body according to the present disclosure and which contains a magnetic fluid, maintains an excellent superparamagnetism, the resin composition molded body can be favorably used for various applications.

EXAMPLES

Hereinafter, the resin composition of the present disclosure and the like are specifically described with reference to Examples; however, the embodiment of the present invention is by no means limited to these Examples. Hereinafter, "%" represents "% by mass", unless specified otherwise.

Example 1

1. Preparation of Resin Composition 3 g of a magnetic fluid (A1, trade name: EXP. 12038, manufactured by Ferrotec Corporation, magnetic particles covered with a dispersant (average particle diameter: 15 nm, magnetic particle: magnetite, dispersant: sodium oleate), dispersion medium: isoparaffin, content percentage of dispersion medium 80%) and 7 g of an epoxy resin having NBR as the specific partial structure (B1, an NBR modified epoxy resin (trade name: EPR 2000, manufactured by ADEKA CORPORATION, epoxy equivalent weight 215 g/equivalent) were stirred in a vessel made of aluminum, to obtain a resin mixture (process A).

The resin mixture thus obtained was heated to a temperature of 80° C., while stirring in the vessel made of aluminum, and then the resin mixture was heated and mixed for 30 minutes, while maintaining the temperature at 80° C. Due to heating, the dispersion medium in the magnetic fluid was removed, and as a result, the weight of the resin mixture became 7.7 g. From the above, it is thought that equal to or higher than 95.8% by mass of the dispersion medium was removed in the process A.

The resulting resin mixture was left to stand to cool down to room temperature (at 25° C.), and then 1.96 g of a curing agent (D1: polyalkyleneoxydiamine, trade name: JEFFAMINE D-230, manufactured by Huntsman Chemical Co.) were added thereto, to obtain 9.66 g of a resin composition (process B).

The content of the magnetic particles in the resulting resin composition was 25% by mass, with respect to the total amount of the resin composition. Further, the content of the dispersion medium contained in the resin composition was measured in a manner as described below, and it was revealed that the content of the dispersion medium was 1.0% by mass.

(Method for Measuring Content of Dispersion Medium)

The content of the dispersion medium contained in the resin composition was measured according to the following method.

(1) The mass (g) of the resin mixture obtained in the process A was measured. Thereafter, the mass (g) of the resin mixture that had been heated and mixed for 30 minutes, while maintaining the temperature at 80° C., was measured. The difference between the measured values was designated as the decrease amount (g) of the dispersion medium.

(2) Since the content percentage of the dispersant with respect to the total mass of the magnetic fluid used in the process A is 80% by mass, the contained amount of the dispersion medium in the magnetic fluid, that is, the contained amount (g) of the dispersion medium contained in the resin mixture was calculated according to the following equation.

Contained amount (g) of dispersion medium contained in resin mixture=Contained amount (g) of magnetic fluid×0.8

(3) From the resulting contained amount (g) of the dispersion medium contained in the resin mixture and the above-described decrease amount (g) of the dispersion medium, the contained amount (%) of the dispersant in the resin composition in the process (B) was determined according to the following equation.

Contained amount (g) of dispersion medium contained in resin composition in process $(B)$= [Contained amount (g) of magnetic fluid×0.8]− [Decrease amount (g) of dispersion medium]

(4) From the value thus obtained, the contained amount (%) of the dispersant in the resin composition in the process (B) was determined according to the following equation.

Content percentage (%) of dispersion medium with respect to resin composition obtained in process $(B)$=[Contained amount (g) of dispersion medium after heating at 80° C./Contained amount (g) of resin mixture after heating at 80° C.]×100

2. Evaluation of Mutual Solubility in Resin Composition

The mutual solubility (uniformity) in the resin composition was evaluated according to the following criteria. The results are shown in Table 1.

As a result, in the resin composition of Example 1, the mutual solubility was favorable. After preparation of the resin composition, even after the laps of one week, the resin composition was a uniform composition.

—Evaluation Criteria—

A: After preparation, even after the laps of 1 week, mutual solubility is favorable, and the resin composition is a uniform composition.

B: After preparation, for 2 days, mutual dissolution is realized; however, after the laps of 1 week, aggregation and separation are observed.

C: In less than 2 days after preparation, aggregation and separation are observed.

3. Measurement of Magnetic Hysteresis

With regard to the resin composition obtained in the process B, the M-H curve which shows the relationship between the magnetization (magnetic polarization) M [T] and the magnetic field strength H [A/m] was measured using a vibrating sample magnetometer (VSM) VSM-5-15 (manufactured by TOEI INDUSTRY CO., LTD.) and converted to a B-H curve, which shows the relationship between the magnetic flux density B [T] and the magnetic field strength H [A/m] using the constant described below. The B-H curve was observed, whereby the presence or absence of magnetic hysteresis was observed.

$$B = \mu_0 H + M$$

In the above equation, $\mu_0$ is called absolute permeability of vacuum and is a constant of $4\pi \times 10^{-7}$ (H/m).

Note that, the measurement of magnetic hysteresis was carried out with regard to only the resin compositions which were evaluated as A or B in the evaluation of mutual solubility.

—Evaluation Criteria—

A: In the B-H curve, magnetic hysteresis is not observed.

B: In the B-H curve, magnetic hysteresis is observed.

As a result, in the resin composition of Example 1, magnetic hysteresis was not observed. It is understood the resin composition of Example 1 had excellent magnetic properties.

4. Production of Resin Composition Molded Body 5 g of the obtained resin composition was supplied in to a metal mold and was placed in a constant-temperature bath, together with the metal mold. The resin composition was allowed to cure at 80° C. for 1 hour. After curing, the mold was released, whereby a resin composition molded body was obtained (process E).

5. Evaluation of Curability of Resin Composition

In the production of a resin composition molded body in the process E, the curability of the resin composition was evaluated according to the following criteria. The results are shown in Table 1.

—Evaluation Criteria—

A: Curing is conducted, whereby a resin composition molded body is obtained.

B: Curing is not conducted, whereby a resin composition molded body is not obtained.

As a result, the resin composition of Example 1 had favorable curability, and a resin composition molded body was obtained.

Example 2 to Example 7

Resin mixtures and resin compositions were obtained in a manner substantially similar to that in Example 1, except that the kinds and the contained amounts of the magnetic fluid, the resin or the precursor thereof, the curing agent, and the additive were changed as described in Table 1 below. Using each of the resin compositions thus obtained, resin composition molded bodies were produced in a manner substantially similar to that in Example 1.

The resin mixtures and resin composition molded bodies thus obtained were evaluated in a manner substantially similar to that in Example 1. The results are shown in Table 1.

Each component shown in Table 1 is the following substance.

B2: CTBN modified epoxy resin (trade name: TSR960, manufactured by DIC Corporation, epoxy equivalent weight 230 g/equivalent to 250 g/equivalent, specific partial structure: CTBN)

B3: Dimer acid-modified epoxy resin, trade name: B-TOUGH A2, manufactured by Croda Japan KK, specific partial structure: dimer acid prepared by dimerizing oleic acid)

B4: 50:50 Mixture of bisphenol F type epoxy resin and bisphenol A type epoxy resin, trade name: ZX-1059, manufactured by NIPPON STEEL & SUMIKIN CHEMICAL CO., LTD., epoxy equivalent weight 165 g/equivalent)

B5: Polyether polyol (trade name: PANDEX GCB41, manufactured by DIC Corporation)

B6: Vinyl group-containing organo polysiloxane (YE5822A, manufactured by Momentive Performance Materials Japan LLC)

D2: Hexamethylene diisocyanate (trade name; PANDEX GCA11, manufactured by DIC Corporation)

D3: H—Si group-containing organo polysiloxane (YE5822B, manufactured by Momentive Performance Materials Japan LLC)

Comparative Example 1

A resin composition of Comparative Example 1 was obtained in a manner substantially similar to that in Example 1, except that, in place of 7 g of the thermosetting resin (B1) including a specific partial structure, which were used in Example 1, 7 g of a dimer acid (C1: trade name: TSUNODYME 395, manufactured by TSUNO CO., LTD.) were added, and a curing agent was not used.

The resin composition thus obtained was evaluated in a manner substantially similar to that in Example 1. The results are shown in Table 1. Note that, since a uniform composition was not obtained, evaluation of magnetic hysteresis and production of a resin composition cured body were not conducted.

Comparative Example 2

A resin composition of Comparative Example 2 was obtained in a manner substantially similar to that in Example 1, except that, in place of 7 g of the thermosetting resin (B1) including a specific partial structure, which were used in Example 1, 6 g of a thermosetting resin (B4) that does not include a specific partial structure and 1 g of a dimer acid (C1) were used. The resin composition thus obtained was evaluated in a manner substantially similar to that in Example 1. The results are shown in Table 1. Note that, since a uniform composition was not obtained, evaluation of magnetic hysteresis and production of a resin composition cured body were not conducted.

Comparative Example 3

A resin composition of Comparative Example 3 was obtained in a manner substantially similar to that in Example 1, except that, in place of 7 g of the thermosetting resin (B1) including a specific partial structure, which were used in Example 1, 7 g of a thermosetting resin (B4) that does not include a specific partial structure were used. The resin composition thus obtained was evaluated in a manner substantially similar to that in Example 1. The results are shown in Table 1. Note that, since a uniform composition was not obtained, evaluation of magnetic hysteresis and production of a resin composition cured body were not conducted.

composition of Comparative Example 2, which individually includes a resin that does not include a specific partial structure in the molecule and a dimer acid, and Comparative Example 3, which includes only a thermosetting resin that does not include a specific partial structure, the mutual solubility between the magnetic fluid and the resin was insufficient, and a uniform resin composition molded body was not obtained.

TABLE 1

| | | | Exp-1 | Exp-2 | Exp-3 | Exp-4 | Exp-5 | Exp-6 | Exp-7 | C. Exp-1 | C. Exp-2 | C. Exp-3 |
|---|---|---|---|---|---|---|---|---|---|---|---|---|
| Resin Composition | Magnetic fluid | A1 | 3 | 3 | 3 | 3 | 6 | 2 | 2.5 | 3 | 3 | 3 |
| | Epoxy resin including a specific partial structure | B1 | 7 | | | | 4 | | | | | |
| | | B2 | | 7 | 3.5 | | | | | | | |
| | | B3 | | | | 1.1 | | | | | | |
| | Epoxy resin including no specific partial structure | B4 | | | 3.5 | 6 | | | | | 6 | 7 |
| | Urethane resin precursor (Polyether polyol) | B5 | | | | | | | 2 | | | |
| | Silicone resin including a specific partial structure (Organo silicone resin including a vinyl group) | B6 | | | | | | | 1.3 | | | |
| | Dimer acid | C1 | | | | | | | | 7 | 1 | |
| Curing agent | Amine | D1 | 2 | 1.8 | 2.1 | 1.8 | 1.1 | | | | 2 | |
| | HDI | D2 | | | | | | 0.2 | | | | |
| Crosslinking agent | Organo silicone including a H-Si group | D3 | | | | | | | 1.3 | | | |
| | Content of magnetic powder (%) | | 25 | 25 | 25 | 25 | 53 | 39 | 40 | 24 | 24 | 24 |
| | Content of dispersion medium (%) | | 1.0 | 3.1 | 2.6 | 2.5 | 1.8 | 3.5 | 6.2 | no Ev. | no Ev. | no Ev. |
| Evaluation | Mutual solubility | | A | A | A | A | A | A | B | C | C | C |
| | Magnetic hysteresis of resin composition | | A | A | A | A | A | A | A | no Ev. | no Ev. | no Ev. |
| | Curability of resin composition | | A | A | A | A | A | A | A | no Ev. | no Ev. | no Ev. |

(Addition amount: g)

In Table 1, the abbreviation "Exp." denotes "Example number", the abbreviation "C. Exp." denotes "Comparative Example number", the abbreviation "no Ev." denotes "no evaluation was made."

In the composition in Table 1 above, the blank represents that the component concerned is not included.

As shown in Table 1, in the resin compositions of Example 1 to Example 6, the mutual solubility between the magnetic fluid and the resin was favorable, and the resin compositions were each a uniform resin composition. Further, in each of the resin compositions of Example 1 to Example 6, magnetic hysteresis was not observed. It is understood that the resin composition of Example 7 is slightly inferior in the mutual solubility as compared to other Examples. However, with regard to the resin composition of Example 7, it is realized that the mutual solubility and the curability are each a level that is not problematic in practical use, as well as magnetic hysteresis is not observed.

Further, it is thought that, in each of the resin compositions of Examples, magnetic hysteresis is not observed, since the magnetic particles are uniformly dispersed in the resin composition. Accordingly, it is understood that, in the resin composition molded bodies obtained by curing each of the resin compositions of Examples as it is, each of the resin compositions containing a curing agent or a cross-linking agent, magnetic hysteresis is not observed similar to the case of the resin composition before curing.

In contrast, in each of the resin composition of Comparative Example 1, which includes a simple dimer acid in place of a resin including a specific partial structure, the resin Further, comparing Example 1 and Comparative Example 2, it is understood that, even if a resin mixture, in which a resin that does not include a specific partial structure and a monomer that includes a specific partial structure are used in combination, is used, effects like the effects shown in the case of using a resin that includes, in a molecular thereof, a specific partial structure are not obtained.

INDUSTRIAL APPLICABILITY

The resin composition according to the present disclosure has favorable curability, and can form a desired molded body. Further, the resin composition molded body obtained by using the resin composition has excellent magnetic properties.

Therefore, the resin composition according to the present disclosure can be preferably used for various molded bodies required to have magnetic properties, conductive coating materials, and the like.

Further, the resin composition and the resin composition molded body according to the present disclosure, the resin composition molded body that is a cured body of the resin composition, are useful for various kinds of electronic components having a problem in terms of magnetic hysteresis and various kinds of components including a transformer, an inductor, a magnetic sensor, ferrite beads, an antenna conductor, and a sensor for electric current detection.

The disclosure of Japanese Patent Application No. 2016-230424 filed on Nov. 28, 2016 is incorporated by reference herein in its entirety.

All publications, patent applications, and technical standards mentioned in this specification are herein incorporated by reference to the same extent as if such individual publication, patent application, or technical standard was specifically and individually indicated to be incorporated by reference.

What is claimed is:

1. A resin composition comprising:
a magnetic fluid that includes magnetic particles, a dispersant, and a dispersion medium;
at least one selected from the group consisting of a curing agent and a cross-linking agent; and
a thermosetting resin that is selected from the group consisting of an epoxy resin, a silicone resin and a polyurethane resin, and that includes, in a molecule thereof, at least one partial structure selected from the group consisting of a diene skeleton, a silicone skeleton, and a resin skeleton containing an alkyl group having from 6 to 30 carbon atoms or an alkylene group having from 6 to 30 carbon atoms, wherein the diene structure has a rubber component structure selected from the group consisting of nitrile butadiene rubber, carboxy group-terminated butadiene nitrile rubber, butadiene rubber and acrylic rubber, the silicone skeleton has a structure derived from an alkenyl group-containing organopolysiloxane, and a content of the dispersion medium with respect to a total amount of the resin composition is from 1% to 5% by mass,
wherein the resin composition exhibits superparamagnetism.

2. The resin composition according to claim 1, wherein the epoxy resin is at least one selected from the group consisting of a rubber-modified epoxy resin, a dimer acid-modified epoxy resin, a trimer acid-modified epoxy resin and a silicone-modified epoxy resin.

3. The resin composition according to claim 2, further comprising a resin or precursor thereof that does not include, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms.

4. The resin composition according to claim 2, wherein a content of the resin composition includes, in a molecule thereof, at least one partial structure selected from the group consisting of the diene skeleton, the silicone skeleton, and the resin skeleton having an alkyl group having from 6 to 30 carbon atoms or an alkylene group having from 6 to 30 carbon atoms, with respect to a total content of resins or precursors thereof incorporated in the resin composition, is from 10% by mass to 100% by mass.

5. The resin composition according to claim 1, further comprising a resin or precursor thereof that does not include, in a molecule thereof, at least one partial structure selected from the group consisting of a diene skeleton, a silicone skeleton, a urethane skeleton, a 4- to 7-membered ring lactone skeleton, an alkyl group having from 6 to 30 carbon atoms and an alkylene group having from 6 to 30 carbon atoms.

6. The resin composition according to claim 5, wherein a content of the resin includes, in a molecule thereof, at least one partial structure selected from the group consisting of the diene skeleton, the silicone skeleton, and the resin skeleton having an alkyl group having from 6 to 30 carbon atoms or an alkylene group having from 6 to 30 carbon atoms, with respect to a total content of resin or precursor thereof incorporated in the resin composition, is from 10% by mass to 100% by mass.

7. The resin composition according to claim 1, wherein a content of the resin composition includes, in a molecule thereof, at least one partial structure selected from the group consisting of the diene skeleton, the silicone skeleton, and the resin skeleton having an alkyl group having from 6 to 30 carbon atoms or an alkylene group having from 6 to 30 carbon atoms, with respect to a total content of resins or precursors thereof incorporated in the resin composition, is from 10% by mass to 100% by mass.

8. A resin composition molded body that is a cured body of the resin composition according to claim 5.

9. A resin composition molded body that is a cured body of the resin composition according to claim 1, wherein the resin composition molded body exhibits superparamagnetism.

10. The resin composition according to claim 1, wherein the resin skeleton containing an alkyl group having from 6 to 30 carbon atoms or an alkylene group having from 6 to 30 carbon atoms is a resin skeleton containing an alkylene group having from 6 to 30 carbon atoms, and the resin skeleton containing an alkylene group having from 6 to 30 carbon atoms includes a partial structure derived from a dimer acid prepared by dimerizing an unsaturated fatty acid or a partial structure derived from a trimer acid prepared by trimerizing an unsaturated fatty acid.

11. The resin composition according to claim 10, wherein the resin skeleton containing an alkylene group having from 6 to 30 carbon atoms includes a partial structure derived from a dimer acid prepared by dimerizing unsaturated fatty acids having from 6 to 30 carbon atoms or a partial structure derived from a trimer acid prepared by trimerizing unsaturated fatty acids having from 6 to 30 carbon atoms.

12. A method for producing a resin composition, the method comprising:
preparing a resin mixture including (i) a magnetic fluid that includes magnetic particles, a dispersant, and a dispersion medium, (ii) at least one selected from the group consisting of a curing agent and a cross-linking agent, and (iii) a thermosetting resin that is selected from the group consisting of an epoxy resin, a silicone resin and a polyurethane resin, and that includes, in a molecule thereof, at least one partial structure selected from the group consisting of a diene skeleton, a silicone skeleton and a resin skeleton containing an alkyl group having from 6 to 30 carbon atoms or an alkylene group having from 6 to 30 carbon atoms, wherein the diene structure has a rubber component structure selected from the group consisting of nitrile butadiene rubber, carboxy group-terminated butadiene nitrile rubber, butadiene rubber and acrylic rubber, the silicone skeleton has a structure derived from an alkenyl group-containing organopolysiloxane, and a content of the dispersion medium with respect to a total amount of the resin composition is from 1% to 5% by mass; and
heating the resin mixture to remove the dispersion medium, to obtain a resin composition that exhibits superparamagnetism.

13. A method for producing a resin composition molded body, the method comprising:
preparing a resin mixture including (i) a magnetic fluid that includes magnetic particles, a dispersant, and a dispersion medium, (ii) at least one selected from the group consisting of a curing agent and a cross-linking agent; and (iii) a thermosetting resin that is selected from the group consisting of an epoxy resin, a silicone resin and a polyurethane resin, and that includes, in a molecule thereof, at least one partial structure selected from the group consisting of a diene skeleton, a silicone skeleton, and a resin skeleton containing an alkyl group having from 6 to 30 carbon atoms or an alkylene group having from 6 to 30 carbon atoms, wherein the diene structure has a rubber component structure selected from the group consisting of nitrile butadiene rubber, carboxy group-terminated butadiene nitrile rubber, butadiene rubber and acrylic rubber, the silicone skeleton has a structure derived from an alkenyl group-containing organopolysiloxane, and a content of the dispersion medium with respect to a total amount of the resin composition is from 1% to 5% by mass;

heating the resin mixture to remove the dispersion medium; and heat molding the resin mixture from which the dispersion medium has been removed, to obtain a resin composition that exhibits superparamagnetism.

* * * * *